US006496557B2

(12) United States Patent
Wilson et al.

(10) Patent No.: US 6,496,557 B2
(45) Date of Patent: Dec. 17, 2002

(54) TWO-DIMENSIONAL SLOT X-RAY BONE DENSITOMETRY, RADIOGRAPHY AND TOMOGRAPHY

(75) Inventors: Kevin E. Wilson, Waltham; Jay A. Stein, Boston; Richard Cabral, Tewksbury; Andrew P. Smith, Medford; Vinnie Quinn, Bedford, all of MA (US)

(73) Assignee: Hologic, Inc., Bedford, MA (US)

( * ) Notice: Subject to any disclaimer, the term of this patent is extended or adjusted under 35 U.S.C. 154(b) by 88 days.

(21) Appl. No.: 09/767,286

(22) Filed: Jan. 22, 2001

(65) Prior Publication Data

US 2001/0048732 A1 Dec. 6, 2001

Related U.S. Application Data

(60) Provisional application No. 60/181,193, filed on Feb. 9, 2000, and provisional application No. 60/226,415, filed on Aug. 18, 2000.

(51) Int. Cl.$^7$ .................................................. A61B 6/00
(52) U.S. Cl. ............................. 378/21; 378/85; 378/11; 378/197; 378/205; 250/370.09
(58) Field of Search ................................ 378/197, 205, 378/98.8, 11, 85, 21; 250/370.09

(56) References Cited

U.S. PATENT DOCUMENTS

| | | | |
|---|---|---|---|
| 5,166,524 A | | 11/1992 | Lee et al. |
| 5,526,394 A | | 6/1996 | Siczek et al. |
| 5,802,137 A | * | 9/1998 | Wilkins .................... 250/363.1 |
| 5,838,765 A | | 11/1998 | Gershman et al. |
| 5,841,833 A | | 11/1998 | Mazess et al. |
| 5,847,398 A | * | 12/1998 | Shahar et al. .......... 250/370.09 |
| 5,850,425 A | * | 12/1998 | Wilkins ................. 250/390.09 |
| 5,850,836 A | | 12/1998 | Steiger et al. |
| 6,196,715 B1 | * | 3/2001 | Nambu et al. ................. 378/11 |

* cited by examiner

*Primary Examiner*—David V. Bruce
*Assistant Examiner*—Pamela R. Hobden
(74) *Attorney, Agent, or Firm*—Cooper & Dunham LLP (57) ABSTRACT

An x-ray system using a slot-shaped detector having n rows and m columns of pixels, where n<<m, and providing a variety of relative motions between a patient table and a source-detector unit, including translation along the length of the table, translation across the table, and rotation about the focal spot, and processing the pixel values in a variety of ways to produce information such a shadow graphic x-ray images, tomosynthetic images of surfaces that need not be planar, and bone density estimates. In another embodiment, tomographic images can be obtained directly, using a post-patient collimator that passes nearly all of the primary beam to the imager while eliminating nearly all of the scatter. A feedback loop can equalize the exposure for selected parts of the image substantially in real time.

14 Claims, 9 Drawing Sheets

TWO-DIMENSIONAL SLOT X-RAY BONE DENSITOMETRY, RADIOGRAPHY AND TOMOGRAPHY

REFERENCE TO RELATED APPLICATION

This patent application claims the benefit of provisional Applications Serial No. 60/181,193, filed Feb. 9, 2000 and No. 60/226,415, filed Aug. 18, 2000, respectfully, which are hereby incorporated by reference.

FIELD

This patent specification is in the field of radiography and tomography for patients or inanimate objects, and in the field of x-ray bone densitometry.

BACKGROUND

Digital radiography has made significant inroads in recent years but it is estimated that more than half of the x-ray imaging procedures still involve film. One of the reasons may be that the cost of a two-dimensional digital detector of the same size as the x-ray film typically used in this country, e.g., 14 by 17 inches, is still quite high. Another reason may be that a flat panel digital x-ray detector of this size may receive scattered radiation that could interfere with quantitative work such as estimating bone density. A chest x-ray system using a two-dimensional flat panel x-ray detector is commercially available in this country from Direct Radiography Corporation of Newark, Del. a subsidiary of the assignee of this patent specification, Hologic, Inc. of Bedford, Mass. See, e.g., U.S. Pat. No. 5,166,524, hereby incorporated by reference.

In bone densitometry using penetrating radiation such as x-rays, one-dimensional arrays of detectors have been used, for example in the QDR series bone densitometers commercially available in this country from the assignee of this patent specification, Hologic, Inc. of Bedford, Mass. See, e.g., U.S. Pat. Nos. 5,838,765 and 5,850,836, which are hereby incorporated by reference. In addition, devices that use two-dimensional flat panel detectors for other purposes, such as for fluoroscopy, can be adapted for use in bone densitometry, as in the case of small C-arm x-ray fluoroscopy systems commercially available in this country from FluoroScan Imaging Products, Inc. of Northbrook, Ill., also a subsidiary of Hologic, Inc.

The use of a two-dimensional array of detector elements has been proposed in mammography, in a scanning system. See, e.g., U.S. Pat. No. 5,526,394. The use of two rows of low-energy and high energy-detectors has been proposed for x-ray bone densitometry and baggage inspection. See, e.g., U.S. Pat. No. 5,841,833.

Film tomography has been used for some time in this country, and typically involves moving an x-ray source on one side of a stationary patient and film at the other side in opposite directions while the patient remains stationary. The source typically emits a cone-shaped or pyramid-shaped x-ray beam. In the course of imaging, a planar region in the patient that is often called the focal plane and is parallel to the film, is in better focus in the image while the rest of the patient's body is more blurred. The image is not very clear, but can still be diagnostically useful in some cases.

It is believed that a need remains for a system using a two-dimensional detector in a manner that would be more effective than the known prior art proposals, and certain aspects of the system and method disclosed herein is directed to meeting such a need. Further, it is believed that improvements in tomography are desirable, and certain aspects of the system and method disclosed herein are directed to meeting such a need. While the disclosure below is mainly in the context of patient examination, the system can be used to examine inanimate object as well, such as in baggage or product inspection.

SUMMARY

Certain embodiments of the x-ray system disclosed in this patent specification use a two-dimensional, slot-shaped detector of x-rays, e.g., a 25×1 cm detector that has pixel size of approximately 100 micrometers and is scanned along the image plane but also can rotate about the focal point of the x-ray source and can move along the x-ray propagation direction relative to the patient. The pixel values can be processed to obtain tomosynthetic information and for other purposes as well. The focal plane or focal surface that is in best focus is a function of the geometry and other characteristics of the relative motion between at least two of the x-ray source, the patient, and the detector and the number of pixel rows that are shifted before adding pixel values from different time frames. For example, if the detector has n rows and m columns of pixels, and both the x-ray source and the detector scan the patient in a linear motion, one planar or non-planar region (focal plane) in the patient can be kept in effective focus by shifting and adding rows of pixel values. If the system adds the pixel values for pixel row n and time frame 1 to the pixel values for pixel row n+1 and time frame 2, (or row n+2, n+3, . . . ), etc., a tomosynthetic image can be formed that can correspond in principle to the information content of a conventional, film tomographic image obtained by moving the x-ray source and film cassette in opposite directions. If the system disclosed herein uses a pulsed x-ray source, the pulse duration t should be short compared to the speed c of translation of the source/detector such that ct<(pixel size), or at least ct<(desired spatial resolution). Similar consideration applies if the system uses a constant x-ray source, in which case pixel integration (interrogation) time is the parameter of interest. If the system uses a dual-energy pulsed x-ray source or beam, this must be taken into account in any addition of pixel values from different time frames. For example, if the energies alternate in the x-ray pulse train, pixel values from odd frames can be added together for image information for one energy, and pixel values from even frames can be added together for image information pertaining to the other energy. As an alternative to a pulsed dual-energy x-ray source or beam, low-energy detector elements and high-energy detector elements can be used to concurrently measure the high and low x-ray energy, as known in the art.

When the disclosed system is used for a tomosynthetic image, the plane or surface that is in best focus is defined by the geometric formula b=sw/d, where s=distance out of the plane, w=width of the x-ray detector, and d=distance between the x-ray source and detector. Other planes or surfaces in the patient are blurred, which can be desirable as it in effect makes transparent tissue that is away from the plane or surface in focus, but can be undesirable if the tissue of interest extends along the length of the x-ray beam or if the tissue of interest curves out of the plane or surface of interest (as the spine of a person lying on his/her side). It should be understood that in practice the "plane" or "surface" in focus has some thickness in the direction of x-ray propagation, i.e., there is some depth of focus as in conventional photographic exposures. One way to deal with depth of focus issues is to store all pixel values, or at least all that could pertain to the volume or interest, so that any tomosynthetic image can be generated from them as desired so long as it is within the volume for which pixel values were stored, and the user can command the generation of images of different planes when looking for tissue of interest. Significant data storage requirements need to be taken into account in this approach. Another solution is to dynamically track the location of the feature of interest, by varying the depth of the plane or surface that would be in best focus. If the feature is the spine of a patient, such dynamic tracking can select the shift-and-add parameters discussed above so as to keep the spine in best focus, e.g., to make the gaps between the vertebrae the sharpest, or perhaps the pedicles.

Additionally, rotating the x-ray detector about the x-ray source 30 can produce pixel values for a non-tomosynthetic image that can be reconstructed with all projected planes in focus. The system disclosed herein can operate in both modes—with the x-ray detector rotating about the focal spot in the x-ray source (e.g., for high resolution), and with the x-ray source and the x-ray detector moving, for longer scans. In addition, the detector can be moved further away from the patient when desired to further reduce the effect of x-ray scatter, for example for more accurate bone density estimates.

Other aspects of the disclosure herein relate to obtaining tomographic images using a slit-shaped post-patient collimator in a process in which at least two of the x-ray source, the patient, and the imager move relative to each other. The imager can be an x-ray film cassette, or a digital flat panel detector that can be the same size as conventional x-ray film, or a slot detector such as discussed above. When the imager is a film cassette or a larger area flat panel detector, and the source emits a primary beam collimated to a fan-shape by a source-side aperture, the post-patient collimator can be shaped and dimensioned to allow only the primary, fan-shape beam to reach the imager. This collimator can be in the form of a slot in an x-ray opaque material such as lead of suitable thickness to effectively block radiation impinging thereon outside the slot therein. When the imager is a slot-shaped detector, such as the 25×1 cm detector earlier mentioned, the post-patient collimator can be omitted, although it can still be used to absorb some scattered radiation. It is important to note that the post-patient collimator need not have the type of septa conventionally used in Bucky grids, i.e., it can be simply an open slit between two lead plates, or can be a material easily penetrated by x-rays at the relevant energy range. Thus, while a Bucky grid used in conventional radiography can significantly reduce the amount of radiation that would otherwise reach the imager, the post-patient collimator can allow nearly all of the radiation in the primary beam emerging from the patient to reach the imager.

When taking a tomographic image, exposure can be controlled through a feedback loop to avoid overexposure or underexposure at least along a selected path along the image, for example at the image of the patient's spine. This can overcome a problem particularly evident in lateral lumbar/thoracic images, where the lumbar region can require ten to twenty times the x-ray dose of the thoracic region. In a preferred embodiment, this is done in real time, by monitoring the exposure behind the imager during the scan and adjusting the relevant x-ray beam characteristics accordingly. This can involve adjusting one or more of: (1) the current (mA) of the x-ray tube; (2) the voltage (kVp) of the tube; (3) the power (mAs), which can be done by reducing/increasing the duty cycle of the tube, e.g., by turning the x-ray tube off and on rapidly, by changing the scan speed, and/or by changing the beam aperture at the source side that determines the dimensions of the primary x-ray beam; and (4) the filtration through which the x-ray beam passes before impinging on the patient, e.g., by inserting/removing filters or by sliding or rotating or otherwise moving a filter to change the beam attenuation it causes.

DETAILED DESCRIPTION

Figure 1:
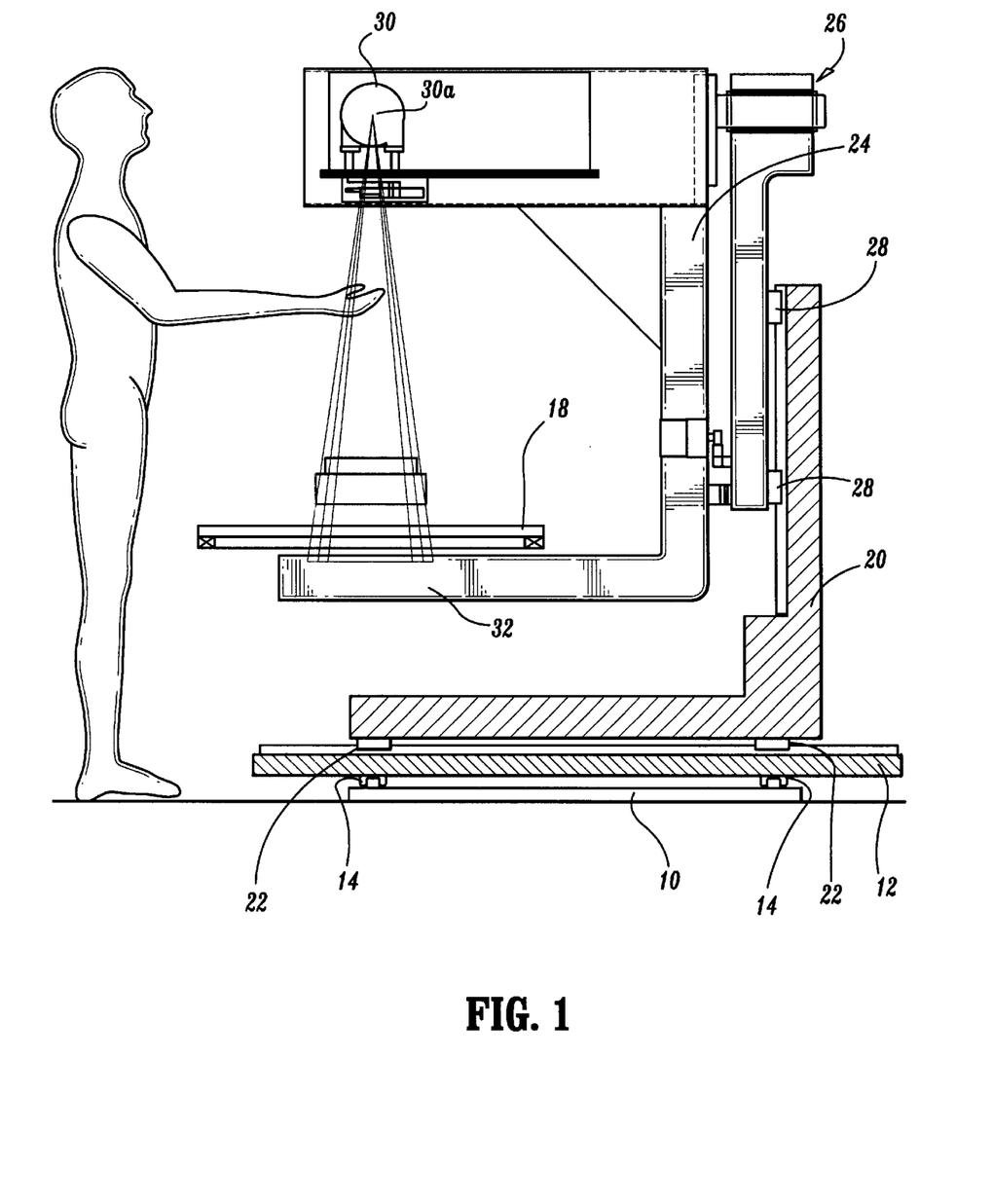
FIG. 1 is a partly schematic a partly sectional side view of a scanner forming a part of an x-ray system.
Figure 3:
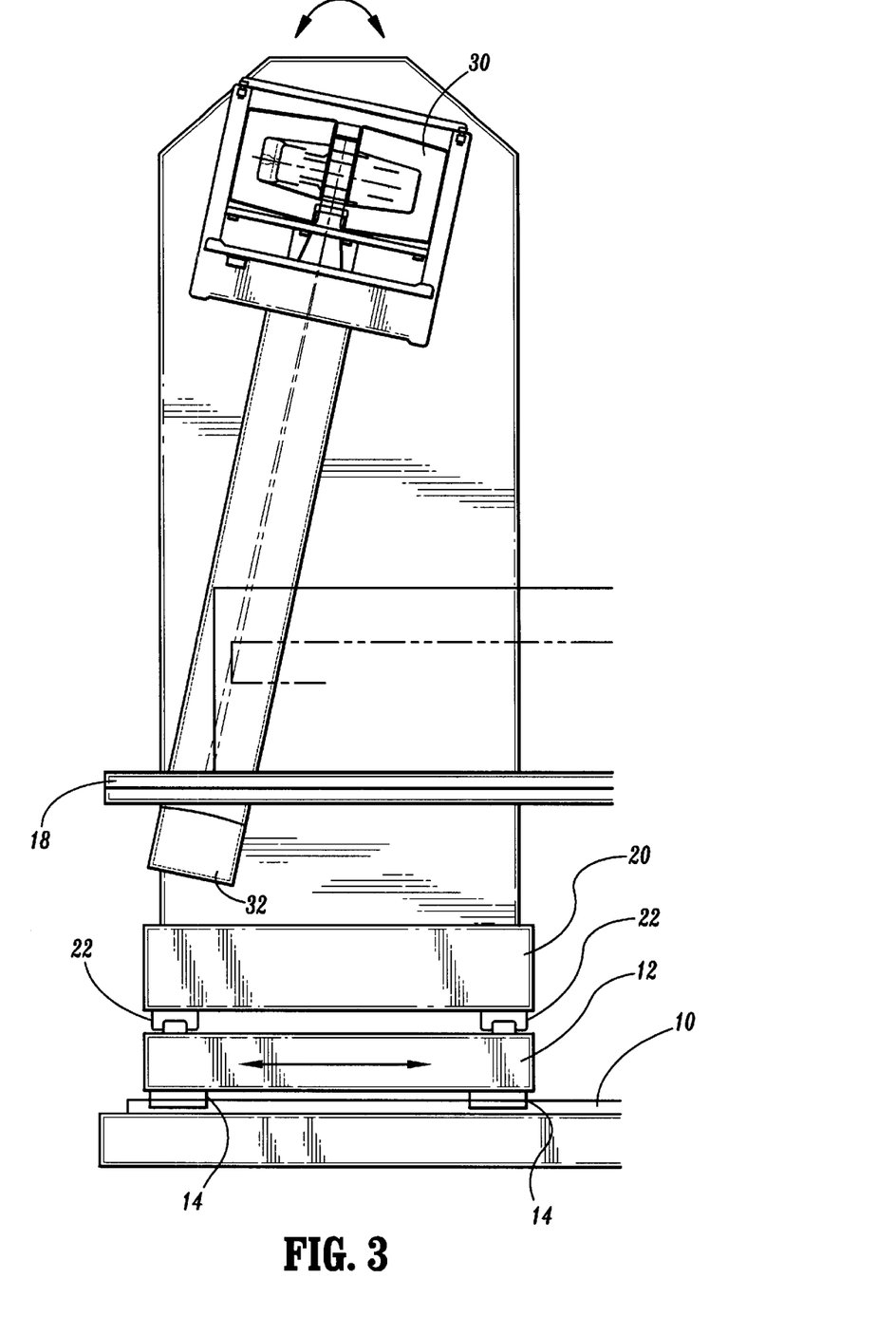
FIG. 3 is a partly schematic and partly sectional front view illustrating the source/detector structure in one position.

Referring to FIGS. 1 and 3, which illustrate an x-ray scanner, one example of the disclosed system comprises a fixed support 10 on which a movable platform 12 rides on rails 14 relative to a patient table 18 along the length of the table, i.e., into and out of the plane of FIG. 1, and left-right in FIG. 3. A gantry support moves on rails 22 relative to patient table 18 along the short dimension of the table, i.e., in a direction transverse to that of the movement of movable platform 12. Two positions of gantry support 20 are illustrated in FIG. 1. Gantry support 20 in turn supports a plate 21 on which a C-arm structure 24 is supported at a bearing 26 and at a curved rail 27 for rotational motion about bearing 26, and is further supported for moving up and down along rails 28. C-arm structure 24 carries an x-ray source 30 producing a collimated, generally pyramid-shaped beam of x-rays and an x-ray detector 32 aligned with x-ray source 30 to receive that x-ray beam. The structure therefore allows scanning a patient on patient table 18 with the x-ray beam along the length of the patient, moving the x-ray beam across the patient, moving x-ray detector 32 further below patient table 18 (and x-ray source 30 down closer to patient table 18), and rotating x-ray source 30 and x-ray detector 32 as a unit about a focal spot 30a in x-ray source 30 from which the x-ray beam emanates and which is aligned with the rotational axis of bearing 26 some or all of the motions described above, or later in this specification, motorized, encode-tracked, and/or computer-controlled.

X-ray detector 32 comprises a two-dimensional array of n rows and m columns of pixels or pixel positions, where n<<m, and the rows extend in a direction across a patient on patient table 18. Any suitable detector technology can be used. For example, detectors available from the following companies can be used: Simage, Trex Enterprises, Suni, and Schick. For example, a detector that is 25 by 1 cm in size and has pixel size of about 0.13 mm can be used, which translates to almost 20,000 pixels. Selected specifications providing further details for an example of a system are set forth below:

| | |
|---|---|
| Focal Spot Size (mm) | 0.8 |
| Source-Detector Distance (mm) | 1067 |
| Detector-Patient Distance (mm) (hi res) | 140 |
| Focal plane distance from detector (mm) | 280 |
| Out of focal plane Image (+/−) (mm) | 30 |
| Source Current mAs | 10 |
| Pulse duration ms | 10 |
| Detector width (mm) | 10 |
| Detector length (mm) | 250 |
| Pixel size (mm) | 0.13 |
| Pixels per mm2 | 59.17 |
| Number of pixels (w*l/pixel) = | 19230.77 |
| Readout time (ms) | 33 |
| Reset time (ms) | 0 |
| ADC Bits | 12 |
| X-ray stopping efficiency | 100.00% |
| Noise per read in X-ray photons | 2.5 |
| Saturation in X-ray photons | 3000 |
| Ouputs | |
| Scan Speed (mm/s) | 13 |
| Scan Time for 150 mm scan (s) | 11.53846154 |
| Number of ave. per detector width (rot) | 4.47 |
| Number of ave. per detector width linear | |
| MBytes per second (MB) | 1.17 |
| Magnification factor (hi res) | 1.15 |
| Magnification factor | 1.36 |
| Penumbra size (mm) (hi res) | 0.12 |
| Penumbra size (mm) (linear) | 0.28 |
| Blurring due to movement hi res | 0.13 |
| Blurring due to movement linear | 0.18 |
| Max tomo smearing in linear scan (mm) | 0.28 |
| Resolution (hi res) SD*3.5 | 0.19 |
| Resolution (linear) SD*3.5 no tomo effect | 0.26 |
| Resolution (linear) SD*3.5 with tomo effect | 0.32 |
| Resolution lp/mm (hi res) | 2.62 |
| Resolution lp/mm (linear) no tomo effect | 1.89 |
| Resolution lp/mm (linear) with no tomo effect | 1.58 |
| Photons per pixel @ 70 kVp-after Al | 489.9 |
| Photons per pixel @ 100 kVp-after Al | 1632.9 |
| Photons per pixel @ 140 kVp-after Al | 682.8 |
| Photons per pixel @ 70 kVp-after patient | 0.5 |
| Photons per pixel @ 100 kVp-after patient | 3.3 |
| Photons per pixel @ 140 kVp-after patient | 3.4 |
| S/N over 1 mm2 no ave, 70 kVp | 1.552935514 |
| S/N over 1 mm2 no ave, 100 kVp | 10.04840626 |
| S/N over 1 mm2 no ave, 140 kVp | 10.505152 |
| S/N over 1 mm2 with max ave, 70 kVp Rot | 3.284108692 |
| S/N over 1 mm2 with max ave, 100 kVp Rot | 21.25011506 |
| S/N over 1 mm2 with max ave, 140 kVp Rot | 22.21602939 |
| Scatter Factor (% of 4 pi) hires | 1.0% |
| Scatter Factor (% of 4 pi) linear | 0.3% |

| | Filtration Al (mm) | Filtration Cu (mm) | Fluence phot/mm2 | Average E (keV) | patient thick (mm) | Fluence phot/mm2 | Average E (keV) |
|---|---|---|---|---|---|---|---|
| @ 70 kVp 1 mAs @ 1 m | 3.8 | 0.08 | 3.30E + 05 | 46 | 300 | 3.40E + 02 | 53.4 |
| @ 100 kVp 1 mAs @ 1 m | 3.8 | 0.08 | 1.10E + 06 | 56 | 300 | 2.20E + 03 | 66.8 |
| @ 140 kVp 1 mAs @ 1 m | 3.8 | 1.58 | 4.60E + 05 | 85 | 300 | 2.30E + 03 | 85 |

Figure 2:
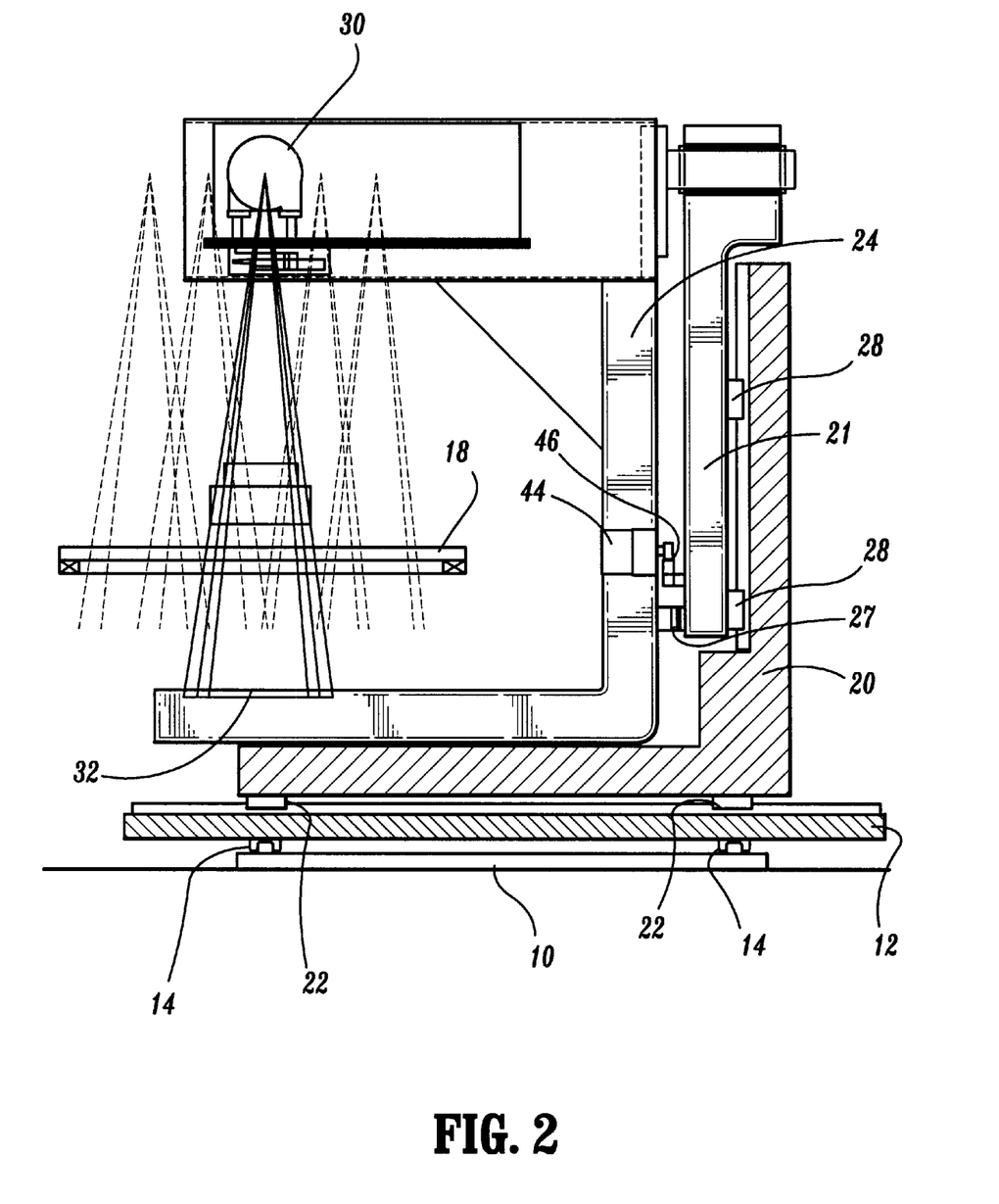
FIG. 2 is similar to FIG. 1 but illustrates different positions of a source/detector structure.
Figure 4:
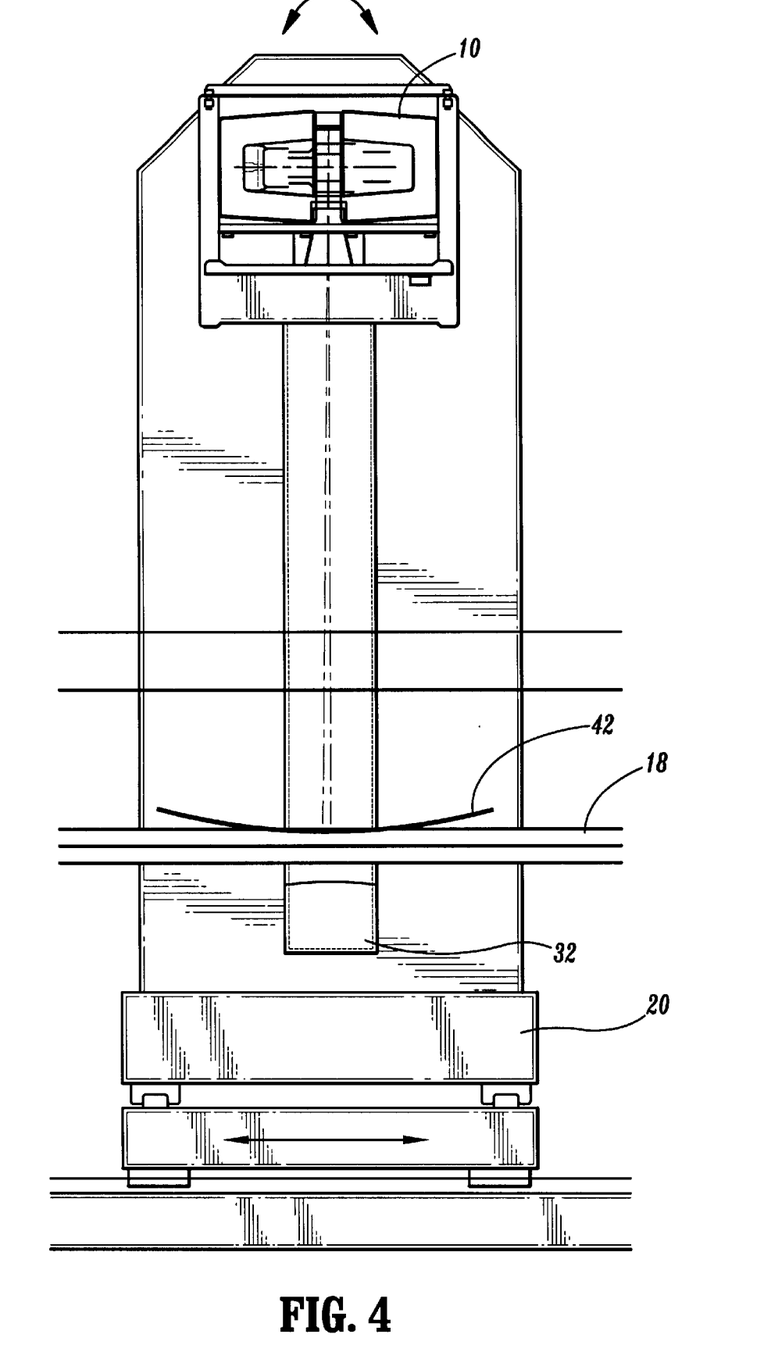
FIG. 4 is similar to FIG. 3 but illustrates the source/detector structure in another position.
Figure 5:
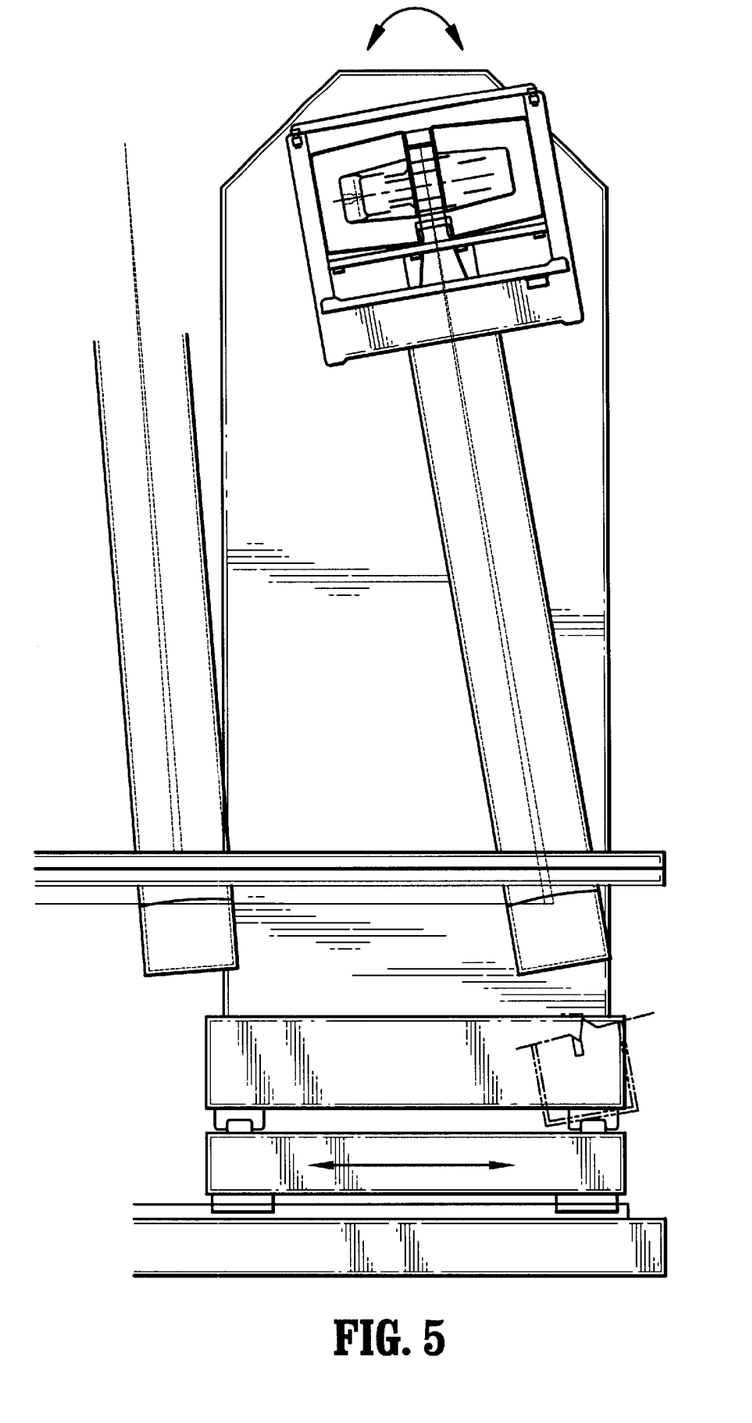
FIG. 5 is similar to FIGS. 3 and 4 but illustrates the source/detector structure in another position.
Figure 7:
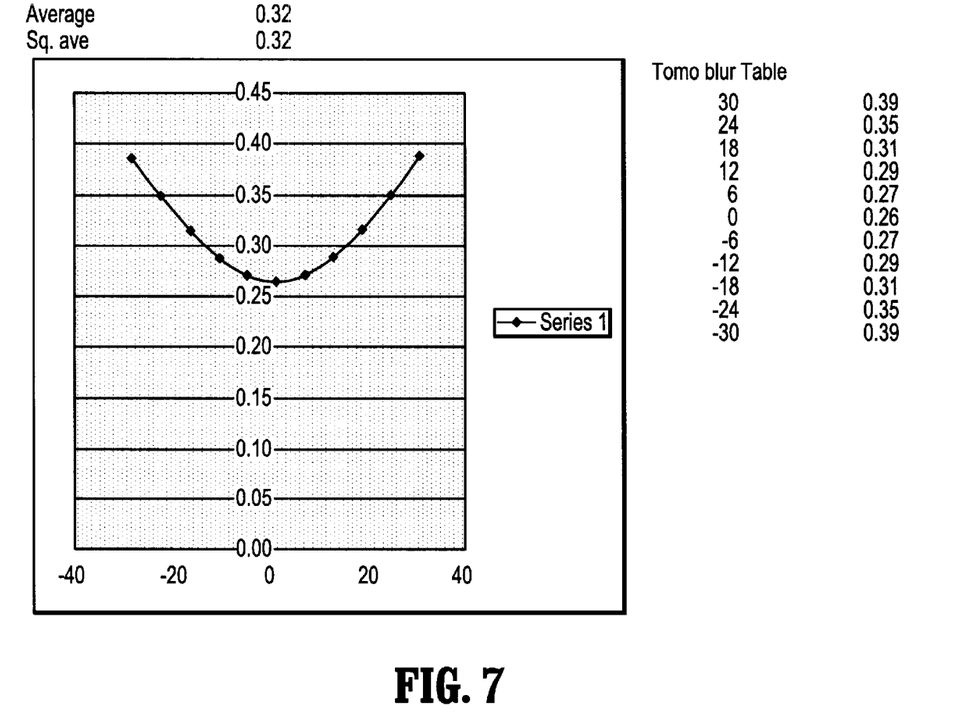
FIG. 7 illustrates blurring factors in tomosynthetic imaging using the system.
Figure 8:
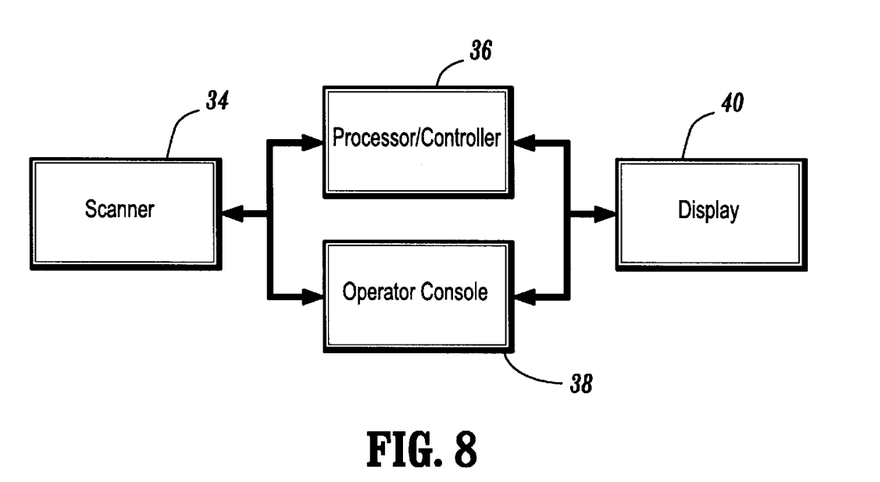
FIG. 8 is a general block diagram of the system.

In operation, a patient on patient table 18 is examined using one or more modes of operation. For a shadowgraphic x-ray image, gantry support 20 moves on rails 22 (see FIGS. 1 and 2) and movable platform 12 moves on rails 14 (see FIGS. 3–5) to select an initial position of the x-ray beam. If desired to angle the beam from its vertical orientation, x-ray source 30 and x-ray detector 32 can be rotated as a unit about focal spot 30*a* (see FIG. 6) to one of the illustrated positions or to a position intermediate those illustrated. If desired to have x-ray detector 32 further down from patient table 18, plate 21 is moved down along rails 28. e.g., from the position in FIG. 1 to the position in FIG. 2 or to an intermediate position. Movable platform 12 then moves along rails 14 relative to patient table 18, along the length of patient table 18, to scan the x-ray beam along a patient thereon. Patient table 18 is separately supported and, if desired, also can move along its length dimension relative to fixed support 10 in the same or opposite direction as movable platform 12, and/or in a direction transverse to the length of patient table 18, either during the scan, or before and/or after the scan. During the scan, the pixels in x-ray detector 32 are read to produce pixel values related to x-rays received thereby over respective integration intervals (frame periods). These pixel values are digitized and sent from scanner 34 (FIG. 8) to a processor 36 that includes computational and control hardware and software to process the pixel values and control the system and interact with an operator console 38 and a display 40 that can comprise a display screen and/or a film/paper printer or other equipment to store and/or display alphanumerical data, graphs and/or images. In general outline, the system is similar to the QDR systems earlier discussed and described in the patents incorporated by reference. The x-ray beam can scan the entire patient, or only a part of interest. If the area of interest is wider than the x-ray beam, two or more successive scans can be carried out, with gantry support 20 and/or the patient table stepped in a direction across the patient, so as to cover the area of interest in a manner similar to that discussed in said U.S. Pat. No. 5,838,765, with appropriate feathering and interpolation of pixel values at the seam for the image information from adjacent scans. The pixel data obtained in this manner can be used to produce an image similar to a conventional x-ray shadowgram. Alternatively, the pixel values can be processed to produce a tomosynthetic image by computationally simulating a spatial shift between focal spot 30*a* and pixels in x-ray detector 32 during scanning. The plane or surface that is in best focus in the tomosynthetic image need not be planar but can be curved such that any point therein is at its own vertical distance from a plane parallel to patient table 18, which can be accomplished by suitably reordering the pixel values before adding them in the array of pixel positions in the image. The degree of blurring versus distance from a selected tomographic plane is illustrated in graph form and in table form in FIG. 7. If dual-energy measurements are taken, images can be formed using the low-energy measurements only, the high-energy measurements only, or both blended in selected proportions. The same pixel data can be used to calculate or estimate quantitative bone parameters such as bone mineral density (BMD) using computational and data processing techniques of the type used in said QDR bone densitometers.

Figure 6:
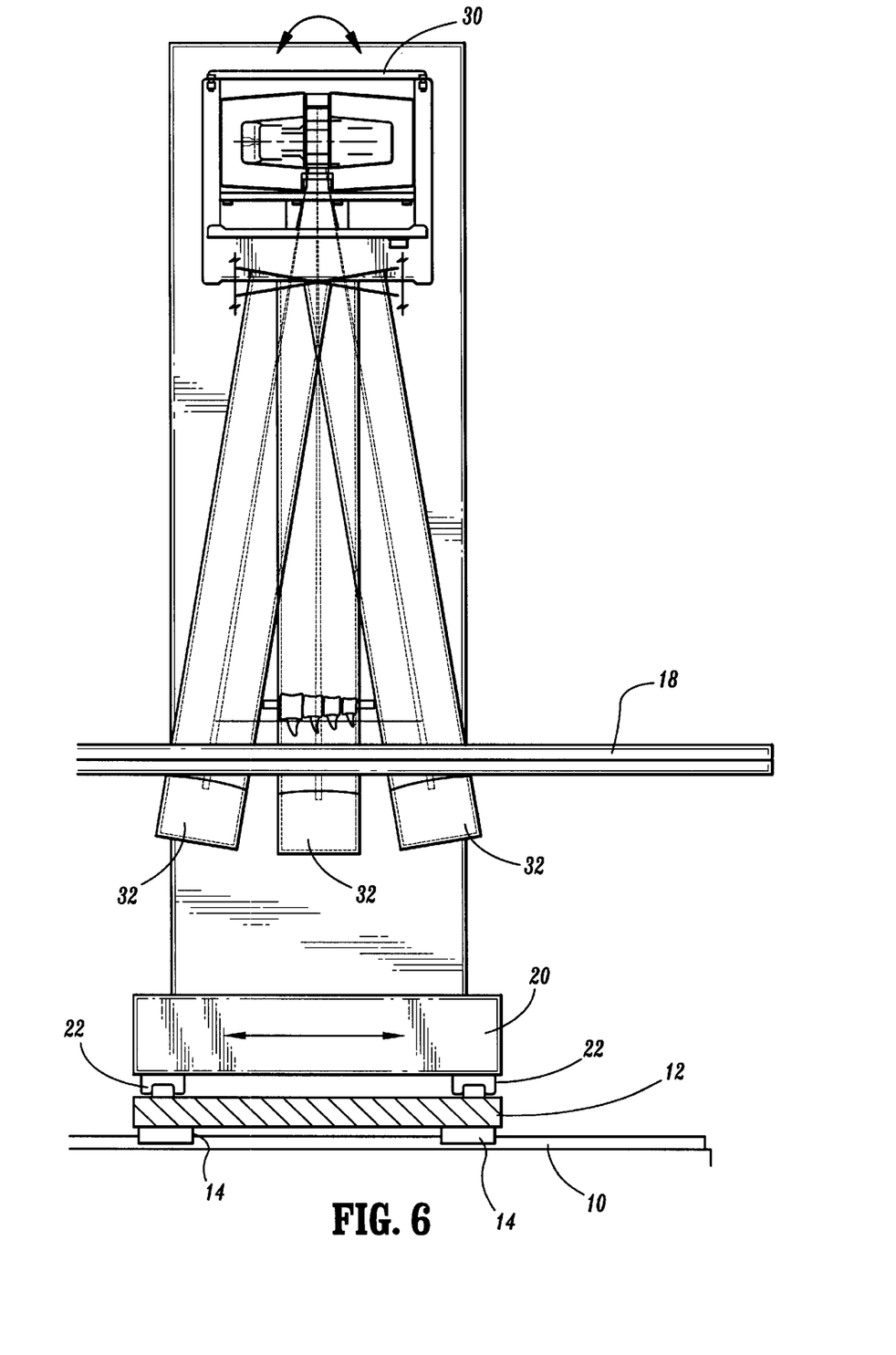
FIG. 6 is similar to FIGS. 3–5 but illustrates a rotational motion of the source/detector structure.

Referring to FIG. 6, in another mode the system can derive pixel values that are particularly suitable for bone densitometry or for high resolution imaging of portions of the patient's body. In this mode, the initial position of the x-ray beam is selected using the motions discussed above, and x-ray source 30 and x-ray detector 32 move as a unit in a rotational motion about focal spot 30*a*. The pixel values of interest are produced during this rotational motion. A curved encoder strip 43 can be used to time the integration periods for the pixels in x-ray detector 32 to the rotational motion thereof so that the integration periods are equally spaced in time, if so desired. A motor 44 can be used to drive C-arm structure 24 in this rotational motion through a rack-and-pinion arrangement 46. The driving arrangements for the other motions are not illustrated but are within the skill of the art and can be similar to those used in said QDR equipment for similar motions. The distance between patient table 18 and x-ray detector 32 can be selected in this mode as well, by moving plate 21 up or down along rails 28, to select the degree of magnification and the degree of the scatter of x-ray that will affect the pixel values.

Figure 9:
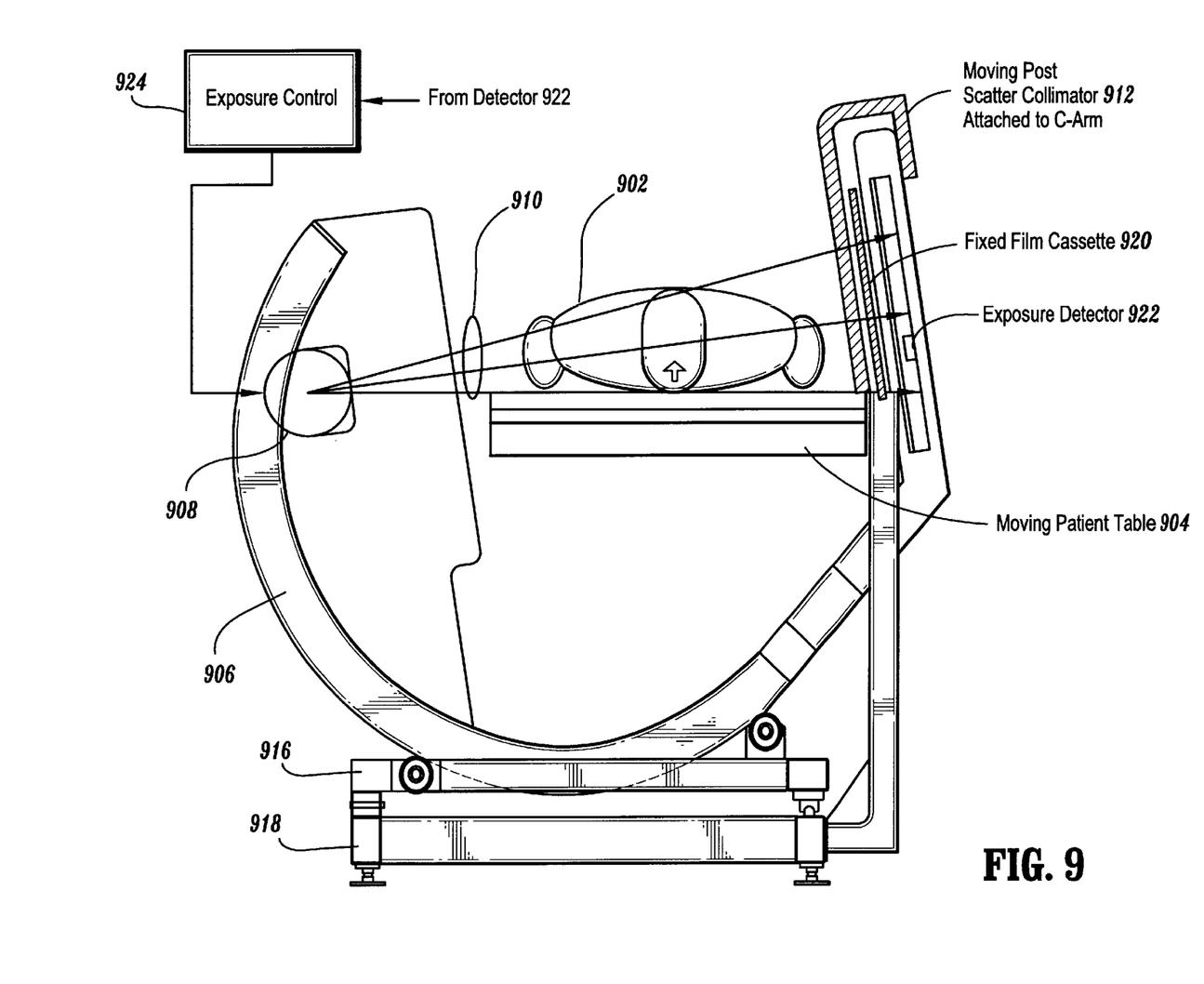
FIG. 9 is a side elevation and part sectional view of an example of a system for obtaining tomographic images, and includes a block diagram of a feedback loop for equalizing x-ray exposure.
Figure 10:
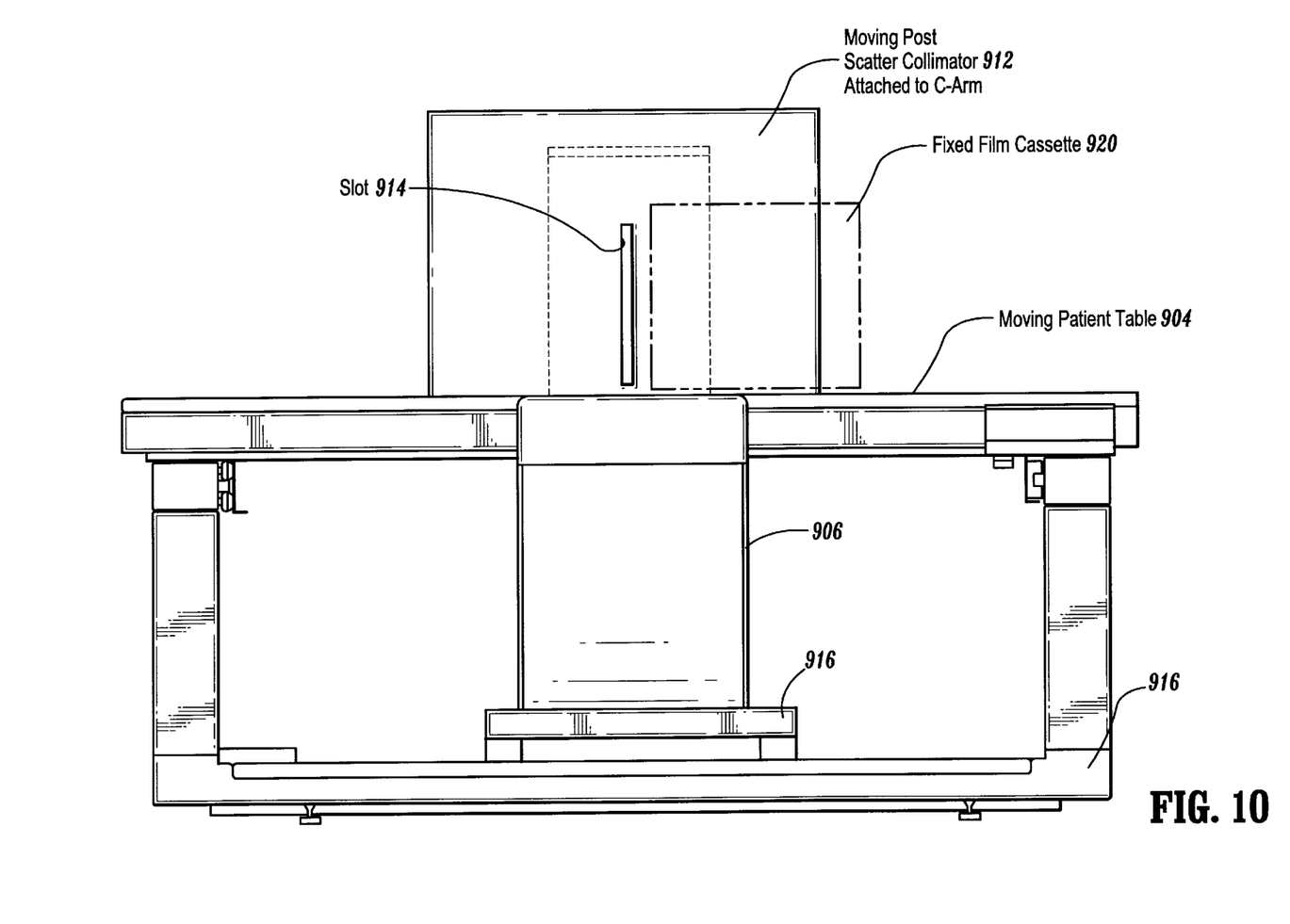
FIG. 10 is a front elevation of the system of FIG. 9.

FIGS. 9 and 10 illustrate another example of a system for obtaining tomographic images. This example is based on a modification of the QDR 4500 system earlier identified. A patient 902 is supine on a patient table 904 which, as in the commercially available QDR 4500 system, is selectively driven along the length of the table (in a direction in or out of the drawing) and across the length of the table (left-right in the drawing) by motors under computer control. A C-arm 906 supports an x-ray source emitting a fan-shaped x-ray beam 910 conforming to a plane parallel to the drawing sheet and directed at patient 902. Beam 910 is shaped by a source-side aperture which is not shown but is used in the commercial QDR 4500 systems and is known in the art, making the beam relatively thin in a direction normal to the sheet of the drawing. As a non-limiting example of approximate dimensions, the source-side aperture is 1 mm wide (in a direction normal to the drawing sheet) and 66 mm tall and is 240 mm from the focal spot in the x-ray tube, and the source-to-detector (S/D) distance is 40 inches. C-arm 906 carries at its other end, across the patient from source 908, a post-patient collimator 912 that has a slit 914 positioned, shaped and dimensioned to receive the primary x-ray beam 910. For example, in the case of the dimensions given above, slot 914 can be approximately 3.8 mm wide (5 times wider that the source-side aperture) and nearly 14 inches tall. Post-patient collimator 912 can be made of an x-ray opaque material such as lead of a suitable thickness (e.g., several mm), sufficient to substantially block the passage through it of radiation other than that in the primary x-ray beam 910. Slot 914 can be simply a cut-out, or it can be material that is essentially transparent to the primary beam 910. To further keep scatter from reaching the imager, collimator 912 can be made thicker, at least at the area immediately surrounding slot 914.

C-arm 906 is supported on a carriage 916 that is selectively driven along the length of patient table 904 by motors under computer control, as in said QDR 4500 system, on a support frame that in turn is supported on the floor. Frame 918 also supports an imager 920 that in this example is a conventional x-ray film cassette. In other examples, imager 920 can be a full size digital flat panel detector having an image surface of, e.g., 14×17 inches, or a slot-shaped digital detector similar to detector 32 in FIG. 1, or some other detector of x-rays.

To obtain a tomographic image that includes, e.g., the spine of patient 902, at least two of source 908, patient 902, and imager 920 move with respect to each other at appropriate speeds and in appropriate directions. As a non-limiting example, and for the dimensions given above, and also assuming the spine is about 10 inches from the x-ray film in imager 920, table 904 (and thus patient 902) moves in a direction along the length of the table at a linear speed of 0.4 inches per second while C-arm 906 (and thus x-ray source 908, x-ray beam 910, and post-patient collimator 312) moves at 1.6 inches per second, while imager 920 remains stationary. Because slot 914 is entirely or at least essentially transparent to x-rays within primary beam 910, nearly 100% of the radiation emerging from patient 902 within the primary beam reaches imager 920 while the blocking material of collimator 912 blocks nearly all the scatter caused by the primary beam. This is in contrast to the typical scatter grid made of lead strips separated by aluminum in such a way that the grid blocks nearly 50% of the primary beam while eliminating about 90% of the scatter. The effectiveness of such a prior art scatter grid is limited by the fact that both the aluminum and the lead attenuate the primary beam and the lead is thin so as not to attenuate the primary beam too much. On the other hand, post-patient collimator 912 transmits essentially all of the primary beam, thus reducing x-ray exposure of the patient for comparable exposure at the imager. Further, because post-patient collimator 912 allows less scatter to reach imager 920, thereby helping improve image contrast, the kVp of the x-ray tube in source 908 can be raised to allow more penetrating x-rays to be used and thus reduce patient dosage even more. With prior art scatter grids, radiologists often if not typically use kVp that is as low as possible within dose limitations to increase image contrast, because low energy x-rays scatter less. However, with the geometry involving post-patient collimator 912 and its slot 914, higher kVp can be used because nearly all scatter is blocked and nearly all of the primary beam from the patient reaches the imager.

When imager 920 is fixed in space while table 904 and post-patient collimator 912 move at respective linear speeds, the plane or surface in the patient that is imaged depends on the difference in the two speeds, and the thickness of that plane or surface is comparable to depth of focus and depends on the width of the primary beam. If a relatively narrow source side aperture of 1 mm is used, a relatively large depth of focus results and the x-ray image is similar to a conventional x-ray picture but is obtained with lower patient dosage. If a wider aperture is used, the depth of focus is less, which can be desirable when visualizing certain structures.

The width of slot 914 in post-patient collimator 912 can be varied to match changes in the width of the source side aperture that defines the primary x-ray beam 910. The aperture and the slot can be ganged, preferably through suitable computer controlled drives, to maintain matching widths when one changes, such that the cross-section of the primary beam.

Another benefit of post-patient collimator 912 is that because it absorbs most of the scatter leaving patient 902 in a direction away from source 908, it substantially reduces radiation in the room, allowing the entire system to be in a room with no shielding or minimal shielding.

In this example, the x-ray source, the post-patient collimator and the patient move while the x-ray image remains stationary. Alternatively, in this embodiment the patient can be kept fixed while the source and the post-patient collimator on the one hand and the imager on the other hand move at respective speeds, as in conventional film tomography. Still alternatively, the x-ray source can be stationary but the patient on the one hand and the x-ray source and the post-patient collimator on the other hand can move at respective speeds. These alternatives can produce comparable tomographic images and are within the scope of the disclosed system and method.

Instead of using an x-ray film cassette, the embodiment of FIGS. 9 and 10 can be modified to use the slot-shaped x-ray detector 32 described in connection with the embodiments illustrated in FIGS. 1–8. When slot detector 32 is used, it size and position correspond to that of slot 914, and detector 32 moves with the primary beam 910 rather than being fixed in space. In this case, post-patient collimator 912 is not essential for forming the tomographic image and can be omitted. However, it can still be used for the purpose of reducing scatter. As earlier discussed in connection with the embodiments of FIGS. 1–8, by shifting and adding pixels of detector 32, for example by using time delay integration (TDI) to reduce read noise as known in the art, the digital detector 32 can simulate a full size (e.g., 14×17 inch digital flat panel x-ray imager). Conversely, the patient can remain stationary, and the digital slot detector 32 can simulate a moving image detector, similar to standard film tomography. In time delay integration (TDI), the charge in each pixel is shifted to the next pixel, and this is continued until the pixel is read out. When the shift is timed at an appropriate interval, the digital slot detector can simulate a full-size flat panel digital detector.

A slot-shaped digital detector 32 used in this manner is preferably sufficiently wide to receive the entire primary beam for the range of expected patients. For thin patients, a thin source side beam aperture can be desirable to give a large depth of focus so as the image the entire thickness of the spine in the direction of beam propagation. For thick patients, it may be desirable to use a wide source side aperture to improve penetration. When a thin source side aperture is used, it may be desirable to use a thinner slot in a post-patient collimator to reduce the effective width of the x-ray detector. The effective size of the x-ray detector can also be reduced electronically, by only reading pixels within the outline of the impinging primary beam.

For the purpose of improving the image by preventing overexposure or underexposure despite large changes in the x-ray thickness of the patient, e.g., between the lumbar and thoracic regions, the disclosed system can include a feedback system as illustrated in FIG. 9. For this purpose, an exposure detector 922 is positioned behind imager 920 and is supported by C-arm 906 so as to remain within the outline of primary x-ray beam 910. Preferably, exposure detector 922 is positioned such that it receives the portion of beam 910 that has passed through the spine of patient 902, but it could be positioned at a different height. Exposure detector 922 can be single detector element or can comprise several detector elements, e.g., four, whose outputs are added or otherwise combined to reduce noise and transient effects. The output of exposure detector 922 is an input to an exposure control 924 that produces an output controlling one or more parameters of x-ray source 908 in a way designed to maintain a substantially constant output of exposure detector 922 substantially in real time. In this example, with detector 922 aligned with the patient's spine, large changes in exposure at the spine in imager 920 are prevented, even as the image transitions from the lumbar spine to the thoracic spine or vice versa. In the example of modifying a QDR 4500 machine to implement the system of FIGS. 9 and 10, the x-ray detector that is a part of that machine can be used as exposure detector 922, by using the output of only some of the existing elements, for example the output of a row or four detector elements.

Maintaining the exposure level along a selected path in the image can be accomplished in a number of ways in the disclosed system. One or more of the following can be used. A first way is to control the mA of the x-ray tube in source 908 depending on the output of exposure control 924. This can be accomplished by changing the tube current. Using current technology, this tends to lag in time. A second way is to change the kVp of the x-ray tube. This maximizes image contrast as lower kVp results in less patient penetration and increased contrast. Changing kVp can be done rapidly (e.g., in millisecond as compared with the seconds it takes to scan the patient with the x-ray beam) so that the exposure at each part of the picture can be optimized. Higher patient dosage can result using this technique as compared with certain other techniques of equalizing exposure. A third way of equalizing exposure is change the mAs. This can be done by increasing/decreasing the duty cycle of the x-ray tube, e.g., turning the tube off and on rapidly, or by changing the scan speed, and/or by changing the size of the source side aperture. All three can be done in milliseconds. This method reduces patient exposure but typically gives less image contrast than the second way. A fourth way is to change filtration of the x-ray beam before it enters the patient, for example by inserting/removing filters in the path of the beam moving a thicker/thinner portion of a filter in the beam, and/or changing the material of the filter.

Two or more of these ways of equalizing exposure at the imager can be combined. For example, methods two and three can be used at the same time to produce a compromise with regard to image contrast and patient exposure.

While the example illustrated in FIGS. 9 and 10 comprises essentially a modification of the commercially available QDR 4500 machine, the system described can be implemented as a special-purpose machine. For example, while in the QDR 4500 machine the C-arm 906 rotates under computer control, this need not be a feature of a special purpose machine for tomographic imaging. Further, it should be clear that features and components of the several different embodiments described above can be combined into a single embodiment, and that other modifications can be made by those skilled in the art within the scope of the disclosure above and the appended claims. For clarity, the description of components and operations of the QDR 4500 machine that are known in the art has been omitted (e.g., power supplies, motors and controls for patient bed motion etc:).

What is claimed is:

1. An x-ray examination process comprising:
    scanning an x-ray beam and a slot-shaped x-ray detector relative to an object penetrated by the beam, while the beam impinges on the detector, and deriving pixel values related to x-rays received during respective time frames at pixel positions arranged in n rows and m columns in the detector, where n<<m;
    processing said pixel values into a tomosynthetic image of a planar or a non-planar surface in the object through a process that comprises selectively shifting information regarding spatial positions for which said pixel values are derived relative to information regarding pixel positions in said image; and
    displaying said tomosynthetic image.

2. An x-ray examination process as in claim 1 including rotating the beam about a selected rotational axis.

3. An x-ray examination process as in claim 2 in which said beam emanates from a focal spot coinciding with said rotational axis.

4. An x-ray examination process as in claim 1 including orienting the beam along a direction selected from a range of directions that includes both vertical and non-vertical directions, and carrying out said scanning thereafter at the selected orientation of the beam, said beam translating relative to the object during said scanning.

5. An x-ray examination process comprising:
    providing an x-ray source and a detector mounted in alignment with each other such that an x-ray beam emanating from the source impinges on the detector after passing through an object subjected to examination;

said source and detector being mounted for motion as a unit relative to the object, said motion selectively including translation relative to the object along a first direction, translation relative to the object along a second direction transverse to the first direction, and rotation about a rotational axis transverse to said first direction and matching a focal spot from which said beam emanates;

scanning the source and detector relative to the object in a selected subset of said motions while detecting x-rays received by the detector within said beam at each of a multiplicity of pixel positions arranged in n rows and m columns, where n<<m, to derive respective pixel values related to x-rays received at said pixel positions in respective time frames;

processing said pixel values to estimate characteristics of portions of said object scanned during said scanning.

6. An x-ray examination process as in claim 5 in which said pixel values are dual-energy pixel values, one set for a lower range of x-ray energies and another set for a higher range of x-ray energies.

7. An x-ray examination process as in claim 6 in which said characteristics of the object comprise numerical bone density estimates.

8. An x-ray examination process as in claim 6 in which said characteristics of the object comprise an image derived from the pixel values for one of the two energy ranges.

9. An x-ray examination process as in claim 6 in which said characteristics comprise an x-ray image derived in a process involving blending the pixel values for the two energy ranges.

10. An x-ray examination process as in claim 6 in which said characteristics comprise a tomosynthetic image of a selected surface that is within the object and is selected from a planar surface and a non-planar surface.

11. A system comprising:

an x-ray source selectively generating an x-ray beam and an x-ray detector aligned therewith to receive x-rays within said beam;

a patient table between the source and the detector;

a support structure carrying said source and detector and selectively moving the source and detector along the length of the table, across the length of the table and up or down;

said support structure further selectively rotating the source and detector as a unit about a selected rotational axis that is transverse to the length of the table;

said detector comprising a slot shaped array of n rows and m columns of pixel positions, where n<<m, each pixel position producing a respective pixel value for each of a succession of time frames during a scanning motion of the source and detector relative to the patient table; and a processor receiving said pixel values and deriving therefrom characteristics of a patient3 s body supported at said table.

12. A method of carrying out tomographic x-ray examination of a patient comprising:

moving with respect to each other at least two of the patient, a fan-shaped x-ray beam entering a first side of the patient, and an x-ray imager at a second side of the patient;

providing a post scatter collimator between the patient and the imager, said collimator having a slot-shaped window matching a cross-sectional shape of the fan-shaped x-ray beam; and controlling the motion of at least two of the patient, the x-ray beam and the imager, while maintaining the x-ray beam and the window in the post scatter collimator in substantial alignment with each other, to form a tomographic x-ray image of a selected surface in the patient.

13. A method as in claim 12 in which the x-ray imager comprises a digital flat panel x-ray detector.

14. A method as in claim 12 in which the window in the collimator is a cut out in a plate of material that outside the window substantially blocks radiation emerging from the patient.

* * * * *